(12) United States Patent
Olalde Rangel

(10) Patent No.: US 8,231,913 B2
(45) Date of Patent: Jul. 31, 2012

(54) ANGINA PECTORIS AND ISCHEMIC HEART DISEASE AND SYNERGISTIC PHYTOCEUTICAL COMPOSITION FOR SAME

(76) Inventor: Jose Angel Olalde Rangel, Caracus (VE)

(\*) Notice: Subject to any disclaimer, the term of this patent is extended or adjusted under 35 U.S.C. 154(b) by 415 days.

(21) Appl. No.: 12/614,546

(22) Filed: Nov. 9, 2009

(65) Prior Publication Data

US 2010/0119629 A1 May 13, 2010

Related U.S. Application Data

(60) Continuation-in-part of application No. 12/613,718, filed on Nov. 6, 2009, now abandoned, which is a continuation-in-part of application No. 12/372,628, filed on Feb. 17, 2009, now Pat. No. 7,682,616, and a continuation-in-part of application No. 12/372,673, filed on Feb. 17, 2009, now Pat. No. 7,682,617, and a continuation-in-part of application No. 11/924,122, filed on Oct. 25, 2007, now Pat. No. 7,618,639, said application No. 12/372,628 is a division of application No. 11/271,940, filed on Nov. 10, 2005, now Pat. No. 7,303,772, said application No. 12/372,673 is a division of application No. 11/271,940, filed on Nov. 10, 2005, now Pat. No. 7,303,772, said application No. 11/924,122 is a division of application No. 11/271,940, filed on Nov. 10, 2005, now Pat. No. 7,303,772.

(51) Int. Cl.
| A61K 36/254 | (2006.01) |
| A61K 36/28 | (2006.01) |
| A61K 36/45 | (2006.01) |
| A61K 36/16 | (2006.01) |
| A61K 36/71 | (2006.01) |
| A61K 36/09 | (2006.01) |
| A61K 36/00 | (2006.01) |

(52) U.S. Cl. ........ 424/728; 424/732; 424/752; 424/726; 424/195.15; 424/737; 424/725

(58) Field of Classification Search .................. None
See application file for complete search history.

(56) References Cited

U.S. PATENT DOCUMENTS

| 6,129,924 | A | 10/2000 | Maurel et al. |
| 6,264,994 | B1 | 7/2001 | Castillo et al. |
| 6,447,814 | B1 | 9/2002 | Lee et al. |
| 6,541,045 | B1 | 4/2003 | Charters et al. |
| 6,544,563 | B2 | 4/2003 | Wuh et al. |
| 6,579,543 | B1 | 6/2003 | McClung |
| 6,746,695 | B1 | 6/2004 | Martin et al. |
| 7,097,862 | B2 * | 8/2006 | Hodge .................. 424/725 |
| 7,303,772 | B2 | 12/2007 | Olalde Rangel |
| 7,381,432 | B2 | 6/2008 | Olalde Rangel |
| 7,390,512 | B2 | 6/2008 | Olalde Rangel |
| 7,416,748 | B2 | 8/2008 | Olalde Rangel |
| 7,498,048 | B2 | 3/2009 | Olalde Rangel |
| 7,553,501 | B2 | 6/2009 | Olalde Rangel |
| 7,553,503 | B2 | 6/2009 | Olalde Rangel |
| 7,604,823 | B2 | 10/2009 | Olalde Rangel |
| 7,608,286 | B2 | 10/2009 | Olalde Rangel |
| 7,618,639 | B2 | 11/2009 | Olalde Rangel |
| 7,625,587 | B2 | 12/2009 | Olalde Rangel |
| 7,658,956 | B2 | 2/2010 | Olalde Rangel |
| 2003/0008048 | A1 | 1/2003 | Winston et al. |
| 2004/0029955 | A1 | 2/2004 | Kouge et al. |
| 2004/0147460 | A1 | 7/2004 | Ramazanov et al. |
| 2004/0161524 | A1 | 8/2004 | Sakai et al. |
| 2004/0185118 | A1 | 9/2004 | Matsushige et al. |
| 2004/0234544 | A1 | 11/2004 | Jager et al. |
| 2005/0048144 | A1 | 3/2005 | Han et al. |
| 2005/0171034 | A1 | 8/2005 | Halevie-Goldman |
| 2005/0238654 | A1 | 10/2005 | Takeda |
| 2006/0035963 | A1 | 2/2006 | Ashwell et al. |
| 2007/0041993 | A1 | 2/2007 | Holcomb-Halstead et al. |
| 2007/0275008 | A1 | 11/2007 | Olalde Rangel |
| 2008/0260771 | A1 | 10/2008 | Olalde Rangel |
| 2008/0267938 | A1 | 10/2008 | Olalde Rangel |
| 2008/0267939 | A1 | 10/2008 | Olalde Rangel |
| 2009/0004302 | A1 | 1/2009 | Cyr |
| 2009/0155377 | A1 | 6/2009 | Olalde Rangel |
| 2009/0196941 | A1 | 8/2009 | Olalde Rangel |
| 2010/0080827 | A1 * | 4/2010 | Palese et al. ............... 424/209.1 |

FOREIGN PATENT DOCUMENTS

| CN | 1511561 A | 7/2004 |
| MX | 266131 | 4/2009 |
| RU | 2319494 | 3/2000 |
| RU | 2319494 | 3/2008 |
| WO | WO00/57690 | 10/2000 |
| WO | WO2007/059441 | 5/2007 |
| WO | PCT/US2010/021905 | 1/2010 |

OTHER PUBLICATIONS

U.S. Appl. No. 12/614,546, filed Nov. 9, 2009, Olalde Rangel.
U.S. Appl. No. 12/705,512, filed Feb. 12, 2010, Olalde Rangel.
U.S. Appl. No. 12/705,525, filed Feb. 12, 2010, Olalde Rangel.
Health Revolution (www.healthrevolution.co.za/herbs/sutherlandia.htm), Feb. 14, 2005.
Olalde, Jose., "The Systemic Theory of Living Systems", Medicina Sistémica, www.adaptogeno.com, pp. 1-20 (2005).
Olalde Rangel., José A., "*The Systemic Theory of Living Systems and Relevance to CAM, Part I: The Theory*", Lecture Series, eCAM 2005:2(1)13-18.
Olalde Rangel., José A., "*The Systemic Theory of Living Systems and Relevance to CAM, The Theory Part II*", Lecture Series, eCAM 2005:2(2)129-137.

(Continued)

*Primary Examiner* — Christopher R. Tate
*Assistant Examiner* — Deborah A. Davis
(74) *Attorney, Agent, or Firm* — Baker & McKenzie LLP

(57) ABSTRACT

Phytoceutical compositions for the prevention and treatment of circulatory disorders, such as Angina Pectoris and Ischemic Heart Disease are taught. A specific combination of extracts of plants is taught, as well as principles for varying the formulations based on categorizing plants into one of three groups, Energy, Bio-Intelligence, and Organization and selecting several plants from each group. Such combinations have synergistic effects as demonstrated by gene expression levels, yet exhibits minimal side effects.

4 Claims, No Drawings

OTHER PUBLICATIONS

Olalde Rangel., José A., "*The Systemic Theory of Living Systems and Relevance to CAM, The Theory Part III*", Lecture Series, eCAM 2005:2(3)267-275.

Williams et al., Selected secondary metabolites from the phytolaccaceae and their biological pharmaceutical significance. Recent research developments in phytochemistry 6:13-68, (2002).

PCT/US06/60794 Search Report, Dec. 5, 2007, Olalde Rangel.

Antoshechkin A., et al., Analysis of the Effects of the Herbal Preparation Circulat on Gene Expression Levels in Cultured Human Fibroblasts. Phytother. Res. 21: 777-789, 2007.

Olalde J., et al., Clinical Outcomes of Diabetic Foot Management with Circulat. Phytother. Res. 22: 1292-1298, 2008.

* cited by examiner

ANGINA PECTORIS AND ISCHEMIC HEART DISEASE AND SYNERGISTIC PHYTOCEUTICAL COMPOSITION FOR SAME

PRIOR RELATED APPLICATIONS

This application is a Continuation-in-Part application of Ser. No. 12/613,718, filed Nov. 6, 2009, which is a Continuation-in-Part of U.S. application Ser. Nos. 12/372,628, filed on Feb. 17, 2009, 12/372,673, filed on Feb. 17, 2009, and 11/924,122, filed Oct. 25, 2007, each of which are Divisionals of U.S. application Ser. No. 11/271,940 filed Nov. 10, 2005, now U.S. Pat. No. 7,303,772.

FIELD OF THE INVENTION

The invention relates to complex phytoceutical formulation used to treat Angina Pectoris and/or Ischemic Cardiopathy. The formulation is a particular combination of plants and/or nutraceuticals and have synergistic effect in combination. Principles for selecting beneficial formulations are also provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process.

This synergistic or additive pharmacological effect can be beneficial by eliminating the problematic side effects associated with the predominance of a single xenobiotic compound in the body. In this respect, researchers have extensively documented how synergistic interactions underlie the effectiveness of a number of phytomedicines. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses.

Additionally, U.S. Pat. No. 7,303,772, also by the inventor herein, demonstrates a synergistic formulation used to treat diabetic lesions, and the same formulation has been proven to provide significant clinical improvement, as well as synergy as measured by extensive gene expression profiling (Olalde et al., 2008, Antoshechkin et al., 2007).

Thus, on the one hand, synthetics may have the required efficacy for disease treatments; however this can be marred by severe side effects. On the other hand, despite the excellent medicinal qualities of many plants, they are individually insufficient to take chronic degenerative diseases into remission.

However, there is mounting evidence to demonstrate that medical plants contain synergistic and/or side-effect neutralizing combinations sufficient to take chronic degenerative disease into remission. Olalde created The Systemic Theory of Living Systems. This theory is axiomatic, and originates from the phenomenological idea that physiological health is based on three factors: E or functional organic energy reserve; I or active biological intelligence; and O which is the integrity of its structure and function. From this theory the applicant developed a treatment strategy called Systemic Medicine (SM)—based on identifying and prescribing phytomedicines and/or other medications that strengthen each factor for elaborating complex formulations for the treatment of chronic degenerative diseases. Systemic Medicine has shown very auspicious results in the treatment of such pathologies.

Thus, what is needed in the art are better treatment regimes with improved patient tolerance, while providing sufficient efficacy. In particular, better treatments for angina pectoris and ischemic heart disease are desired.

SUMMARY OF THE INVENTION

One embodiment of the invention provides an effective, natural composition for treating circulatory diseases. The composition can be used alone, or can be combined with simultaneous use of one or more pharmaceutical compositions. It can be used for the treatment of Angina Pectoris and/or Ischemic Heart disease and the like.

Another embodiment of the invention provides the use of particular herbal blends, as herein described, for the preparation of a medicament for the treatment of Angina Pectoris and/or Ischemic Heart disease.

Another embodiment of the invention provides a method of treatment of Angina Pectoris and/or Ischemic Heart disease comprising administering to a mammal in need of such treatment a therapeutically effective amount of the herbal blends herein described.

A number of known beneficial plants were classified according to their capacity to enhance the three main elements that support overall health: Energy (E), Bio-intelligence (I) and Organization (O). A synergistic effect is expected when all three categories of herbs (E, I, O) are included in a formulation. Thus, another embodiment of the invention is a method of selecting additional disease treating formulations according to these principles.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.2, 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

All herbal components listed in the complex phytoceutical formulation included herein are commercially available standardized High Pressure Liquid Chromatography (HPLC) fingerprinted, hydro-alcoholic (with ethanol solvent) plant extracts. When an amount of a particular ingredient is given it is understood that equivalent ratios of those ingredients can also be used.

Further, although plants are named here according to commonly used nomenclature, with improving taxonomy plants are often reclassified. Whenever a plant is referenced, it includes related species and/or species with similar active ingredients.

The following examples are illustrative only and should not serve to unduly limit the invention.

EXAMPLE 1

Plant Characteristics—Angina Pectoris and Ischemic Heart Disease

*Angelica sinensis* (Dong Quai or Angelica, also *Angelica Archangelia, Angelica Pubescens* and *Angelica Sylvestris*) contains terpenes (terpenes, mainly β-phellandrene, with β-bisabolene, β-caryophyllene, β-phellandrene, α- and β-pinene, limonene, linalool, borneol, acetaldehyde, menthadienes and nitromenthadienes), macrocyclic lactones (including tridecanolide, 12-methyl tridecanolide, pentadecanolide), phthalates (such as hexamethylphthalate), coumarins (especially furocoumarin glycosides such as marmesin and apterin), angelicin and byakangelicin derivatives (osthol, umbelliferone, psoralen, bergapten, imperatoren, xanthotoxol, xanthotoxin, oxypeucedanin and more), as well as various sugars, plant acids, flavonoids and sterols. Increases formation of Nitric Oxide which contributes to endothelium-mediated vasorelaxation, while inhibits the calcium influx producing vascular smooth muscle relaxation. Induces vasodilatation by inhibiting calcium channel and receptor-operated calcium channel, and receptor-mediated Ca(2+) influx and release. Offers angiogenic properties because it up-regulates vascular endothelial growth factor expression, enhances endothelial cell proliferation and stimulate quantity of vessels. Also, promotes vasodilatation because it inhibits the formation of TXA2 and increases the formation of PGI2. The incorporation of this phytomedicine into compositions provides at least 70 active principles in a single therapeutic.

*Acanthopanax senticosus* (Russian Ginseng, Siberian Ginseng, Eleuthero, Devil's Shrub, Touch-me-not, Wild Pepper, Shigoka, *Acantopanacis senticosus*) contains terpenoids (oleanolic acid), glycosides (Eleutheroside A (daucosterin), B1, C-G, I, K, L, M), phytosterols (β-sitosterol), coumarins (Eleutheroside B1 and B3, isofraxidine), polysaccharides (eleutherans), volatile oils, caffeic acid, coniferyl aldehyde, and sugars. It has activity anti-platelet aggregation activity similar to aspirin, as well as antioxidant activity. One of Eleuthero's action mechanism is its vasorelaxant effect endothelium-dependent and mediated by Nitric Oxide and/or endothelium-derived hyperpolarizing factor. Russian Ginseng contains at least 40 active ingredients.

*Rhaponticum carthamoides* (Leuzea, or Maral Root) contains a mixture of compounds called, "levseins." Levseins represents a complex of more than 10 ecdysterones including 20-beta-ecdysterone, makisterone C, 24-dehydromakisterone A, carthamosterone, polypodyne B and ajugasterone C. Researchers extracted and purified various ecdysteroids from *Rhaponticum* and the Soviets manufactured a synthetic version of this powerful substance for their athletes with great success. Soon after, the U.S. version called Mesobolin circulated on the underground market for a long time. Increases ATP synthesis, stimulates activities of enzymes related to tricarboxylic acid cycle, such as succinate dehydrogenase. Also, normalize NADH dehydrogenase activity, enzyme related to the oxidative phosphorylation processes, contributing to buildup the electrochemical potential used to produce ATP. *Rhaponticum* reduces viscosity of the whole blood and plasma and coagulation potencial. Incorporation of this phytomedicine in a composition provides at least 10 active principles in a single therapeutic.

*Panax ginseng* (Chinese ginseng, panax, ren shen, jintsam, ninjin, Asiatic ginseng, Japanese ginseng, Oriental ginseng, Korean red ginseng) main active components are ginsenosides (Ra1, Ra2, Rb1, Rg1, Rd, Re, Rh1, Rh2, Rh3, F1, F2, F3) and panoxosides, which have been shown to have a variety of beneficial effects, including anti-inflammatory and antioxidant effects. Results of clinical research studies demonstrate that *Panax ginseng* may improve psychological function, causes vasodilation; increases resistance to exogenous stress factors. Ginsenosides relax vessels as a consequence of increased endothelium-derived Nitric Oxide production and reduction of the Angiotensin Converting Enzyme activity. *Panax* promotes the proliferation, migration and adhesion of endothelial progenitor cells. Increases vascular endothelial growth factor production and promotes angiogenesis. Ginsenosides can effectively block Homocysteine-induced dysfunction of endothelium-dependent vasorelaxation. Anti-inflammatory: It inhibits iNOS and COX-2 protein expressions, and activates the transcription factor, NF-kappaB. The incorporation of this phytomedicine provides at least 86 active principles in a single therapeutic.

*Panax quinquefolius* (American Ginseng, Anchi, Canadian Ginseng, Five Fingers, Ginseng, American, North American Ginseng, Red Berry, Ren Shen, Tienchi) is related to *Panax ginseng*, but is a distinct species with higher levels of ginsenoside Rb1 and without ginsenoside Rf. Research suggests that several of ginseng's active ingredients also have a beneficial influence on platelet aggregation. It also demonstrates an anti-atherosclerotic action, apparently mediated by a correction in the imbalance between prostacyclin and thromboxane. Other studies that have found panaxynol or the lipophilic fraction to be the most potent anti-platelet agent in ginseng, chiefly due to an inhibition of thromboxane formation. This possibly occurs via regulation of cGMP and cAMP levels and prolongation of the time interval between fibrinogen to fibrin conversion. Ginsenosides have also been shown to be relatively potent platelet activating factor antagonists. It has antioxidant, anti-inflammatory, and hypolipidemic effects. Increases ATP synthesis by stimulating activities of enzymes related to tricarboxylic acid cycle and oxidative-phosphorylation, such as succinate dehydrogenase, malate dehydrogenase, citrate synthetase, cytochrome oxidase, and phosphorylase. The incorporation of this phytomedicine into a composition provides at least 206 active principles in a single therapeutic.

*Pfaffia paniculata* (Suma, Brazilian Ginseng, Pfaffia, Para Toda, Corango-acu; also *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), pfaffic acids, phytosterols (sitosterol and estimasterol). It also contains saponins. Its germanium content probably accounts for its properties as an oxygenator at the cellular level, and its high iron content may account for its traditional use for anemia. This herb increases oxygenation at the cellular level. It also has anabolic activity at the muscular and cardiac levels by improving the contraction of the myocardia and diminishing arrhythmias and stabilizing the membranes of cardiac cells. Increase ATP synthesis, stimulates activities of enzymes related to tricarboxylic acid cycle, such as succinate dehydrogenase. Also, normalize NADH dehydrogenase activity, enzyme related to the oxidative phosphorylation processes, contributing to buildup the electrochemical potential used to produce ATP. The incorporation of this phytomedicine provides 44 active principles in a single therapeutic.

*Rhodiola rosea* (Golden Root, Roseroot) consists mainly of phenylpropanoids (rosavin, rosin, rosarin (specific to *R. rosea*), phenylethanol derivatives (salidroside, rhodioloside, tyrosol), flavanoids (catechins, proanthocyanidins, rodiolin, rodionin, rodiosin, acetylrodalgin, tricin), monoterpenes (rosiridol, rosaridin), triterpenes (daucosterol, beta-sitosterol), and phenolic acids (chlorogenic and hydroxycinnamic, gallic acids). It also contains organic acids (gallic, caffeic, and chlorogenic acids) and p-Tyrosol. There are many species of *Rhodiola*, but it appears that the rosavins are unique to *R. Rosea*, and it is the preferred species. This herb activates the synthesis or resynthesis of ATP in mitochondria and stimulates reparative energy processes. It also has properties of vasodilatation by activation of mu-opiate receptors in heart muscle, and it is a hypolipidemic, diminishing cholesterol and triglyceride levels. It inhibits angiotensin I-converting enzyme. Induces biosynthesis and increases level of endogenous opioid peptides which, as it's known, act on opioid receptors at the central and periferic level, regulating vascular status. Increases levels of vascular endothelial growth factor. The incorporation of this phytomedicine provides at least 20 active principles in a single therapeutic.

*Echinacea angustifolia* or *purpurea* (Black Sampson, Purple Coneflower, Rudbeckia, Missouri Snakeroot, Red Sunflower) contains alkaloids (Isotussilagine, tussilagine), amides (echinacein, isobutylamides), carbohydrates (echinacin, polysaccharides (heteroxylan and arabinogalactan), inulin, fructose, glucose, pentose), glycosides (echinacoside), terpenoids (Germacrane), Cichoric acid, betaine, methylpara-hydroxycinnamate, vanillin, phytosterols, and volatile oils. *Echinacea* possesses anti-inflammatory properties due to IL-2 production reduction; and down-regulation of COX-2 expression. This plant has been the subject of hundreds of clinical and scientific studies which have primarily used an extract of the root and aerial portions of the botanical. The rich content of polysaccharides and phytosterols in *Echinacea* have cortisone-like actions which can help control inflammatory reactions. The incorporation of this phytomedicine into compositions provides at least 70 active principles in a single therapeutic.

*Ganoderma lucidum* (Reishi, also *G. tsugae, G. valesiacum, G. oregonense, G. resinaceum, G. pfezfferi, G. oerstedli,* and *G. ahmadii*) is an edible fungus containing bitter triterpenoids (ganoderic acid), β-D-glucan, coumarins, alkaloids and ergosterols. Its active principles decrease LDL oxidation and monocyte adhesion to endothelium. Its beneficial effect appears to be multifactorial, including antilipid, vasodilator, antiplatelet, improved hemorheology and the modulation of immunocirculatory balance. It has vasodilator effect and is useful in the treatment of angina. It is hypolipidemic and anti-artherotic. It contains at least 32 active principles.

*Grifola frondosa* (Maitake, Dancing Mushroom; also *G. sordulenta, Polyporus umbellatus* and *Meripilus giganteus*) contains the primary polysaccharide, β-D-glucan in the 1.3 and 1.6 forms. It also contains alpha glucan, lipids, phospholipids, and ergosterol. Animal studies suggest maitake may lower serum cholesterol and triglycerides. Beta-D-glucan is also recognized as an effective immuno-stimulator. *Grifola* is an anti-inflammatory: because it inhibits cyclooxygenase (COX) enzyme; with vasodilation properties due to modulation of the renin-angiotensin system. The incorporation of this phytomedicine provides at least 6 active ingredients for therapeutic use.

*Hydrastis canadensis* (golden seal, yellow root, turmeric root) contains mainly isoquinoline alkaloids (xanthopuccine, berberine, hidrastine, hidrastanine, beta-hydrastine, canadine and canadaline). These confer anti-inflammatory and vasodilator effects. It produces vasodilatation by inhibiting smooth muscle contraction, and inhibiting platelet aggregation. It possesses antiinflammatory properties due to a prostaglandin E2 production reduction as a result of AP-1 binding inhibition. This plant provides at least 34 active principles for therapeutic use.

*Petiveria alliacea* (Anamú, Apacin, Apacina, Apazote De Zorro, Aposin, Ave, Aveterinaryte, Calauchin, Chasser Vermine, Congo Root, Douvant-douvant, Emeruaiuma, Garlic Guinea Henweed, Guine, Guine, Guinea, Guinea hen leaf, Gully Root, Herbe Aux Poules, Hierba De Las Gallinitas, Huevo De Gato, Kojo Root, Kuan, Kudjuruk, Lemtewei, Lemuru, Mal Pouri, Mapurit, Mapurite, Mucura-caa, Mucura, Mucuracaa, Ocano, Payche, Pipi, Tipi, Verbena Hedionda, Verveine Puante, Zorrillo) contains Allantoin, Arborinol, Arborinoliso Astilbin, Benzaldehyde, Benzoicacid Benzyl-2-hydroxy-5-ethyl-trisulfide, Coumarin, Dibenzyl Trisulfide, Engeletin, alpha Friedelinol, Isoarborinol, Isoarborinol-acetate, Isoarborinol-cinnamate, Isothiocyanates, Kno3, Leridal, Leridol, Leridol-5-methyl Ether, Lignoceric Acid, Lignoceryl Alcohol, Lignoceryl Lignocerate, Linoleic Acid Myricitrin, Nonadecanoic Acid, Oleic Acid, Palmitic Acid, Pinitol, Polyphenols, Proline, trans-n-methyl-4-methoxy, Senfol, β-Sitosterol, Stearic Acid, Tannins, and Trithiolaniacine. Its therapeutic properties include anti-inflammatory activity. This phytomedicine provides about 25 active principles.

*Sutherlandia frutescens* (Cancer Bush, also *Sutherlandia Microphylla*) contains L-canavanine, pinitol, GABA (gamma aminobuteric acid), and asparagine. In addition, novel triterpenoid glucoside known as "SU1" has been isolated and characterized. The therapeutic indications include anti-inflammatory, antioxidant and vasodilator effects. *Sutherlandia* achieves anti-inflammatory properties because it inhibits COX-2, and through activation of activator protein-1 (AP-1). This phytomedicine provide at least 5 active principles.

*Tabebuia avellanedae* (Pau d'arco, Ipê, Lapacho, Tahuari, Taheebo, Trumpet Tree, Tabebuia Ipê, Tajy; also *T. ipe, T. nicaraguensis, T. schunkeuigoi, T. serratifolia, T. altissima, T. palmeri, T. impetiginosa, T. heptaphylla, Gelseminum avellanedae, Handroanthus avellanedae, H. impetiginosus, Tecoma adenophylla, Tec. avellanedae, Tec. eximia, Tec. impetiginosa, Tec. integra, Tec. ipe*) extracts contain diverse quinone derivatives and a small quantity of benzenoids and flavonoids, including beta-lapachone, xyloidone, tabebuin, quercetin, tecomine, and steroidal saponins. One important ingredient is lapachol, a derivative of which was patented in 1975. It inhibits NO, iNOS, COX-2 and PGE(2) release. Attenuates expression of mRNA and pro-inflammatory cytokines proteins, such as interleukin (IL)-1beta, IL-6 and tumor necrosis factor (TNF)-alpha. Suppresses NF-kappaB activation by blocking IkappaBalpha degradation and down-regulating ERK, p38 mitogen-activated protein kinase (MAPK) and Akt pathway. The incorporation of this phytomedicine into a composition provides at least 32 active principles in a single therapeutic.

*Uncaria tomentosa* (Cat's Claw, Peruvian Cat's Claw, Samento, Saventaro, Uña de Gato, also *Uncaria guianensis*) has several alkaloids including pentacyclic oxindole alkaloids (POA) (isomitraphylline, isopteropodine, mitraphylline, pteropodine, speciophylline, uncarine F), tetracyclic oxindole alkaloids (TOA) (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidins (OPC). It is an antiinflammatory, vasodilator, and antioxidant. In laboratory testing, rynchophylline displays an ability to inhibit platelet aggregation and thrombosis, suggesting that cat's claw may be useful in preventing strokes and reducing the risk of heart attack by lowering blood pressure, increasing circulation, inhibiting formation of plaque on arterial walls and formation of blood clots in the brain, heart and arteries. Its anti-inflammatory activity is achieved by a TNFalpha and PGE2 production inhibition. This phytomedicine provides at least 10 active ingredients.

*Crataegus oxyacantha* (Hawthorn, see also *C. monogyna*) contains mainly flavonoids (such as flavonoglycosyls, hyperoside, rutin, kaempferol, quercetin) and oligomeric procyanadins (1-epicatechol), which flavonol relaxes arterial walls and decrease peripheral vascular resistance. Also contains amines (phenyletylamine, tyramine, O-methoxyphenethylamine), flavone (apigenin, luteolin) derivatives, vitexin glycosides, tannins, saponins, and cyanogenetic glycosides. *Crataegus* causes endothelium-dependent NO-mediated vasorelaxation associated with cyclic GMP production. Can inhibit angiotensin I-converting enzyme. Inhibits biosynthesis of vasoconstrictors such as thromboxane A2. The incorporation of this phytomedicine into a composition provides at least 52 active principles in a single therapeutic plant.

*Croton lechleri* (Dragon's blood, Sangre de Grado, Sangre de Agua; also *C. draconoides, C. palanostigma, C. erythrochilus C. salutaris,* and *C. gossypifolius*) produces a distinctive red exudate from its trunk containing a considerable amount of secondary plant metabolites, the majority of which are hydrolyzing flavonoids, proanthocyanidins (mainly catechin, epicatechin, gallocatechin and/or galloepicatechin), as well as taspine. Other components include the dihydrobenzofuran lignan, six simple phenols and their derivatives, three steroids, non-saturated fatty acids, diterpenoids (hardwickiic acid, bincatriol, crolechinol, crolechinic acid, coberine A, coberine B) and diterpenoids. It heals wounds and ulcers of vascular origin. Incorporation of this phytomedicine into a composition provides at least 23 active principles in a single therapeutic.

*Ginkgo biloba* (*Ginkgo*) contains ginkgolides, bilobalides, bioflavones and flavone glycosides. Flavone glycosides include quercetin, 3-methylquercetin and kaempferol. Quercetin, myrcetin and the rest of the flavonoid fraction of the extract have antioxidant and free radical scavenger effects. The flavonoids diminish infiltration by neutrophils and increase blood flow. Their antioxidant properties and membrane stabilizing activity increase the tolerance to hypoxia. They improve cellular metabolism and protect against the damage caused by ischemia. Ginkgolide B is a powerful inhibitor of platelet activating factor (PAF), binding to its membrane receptors, and antagonizing platelet aggregation. Similarly, it has anti-inflammatory effect by decreasing vascular permeability, and has vasodilator activity by inhibiting the liberation of thromboxane B2 and prostaglandins. Controlled double blind clinical studies conclusively demonstrate the effectiveness of *Gingko biloba* in treating peripheral arterial insufficiency. *Ginkgo* induces the production of vascular endothelial growth factor and up-regulates the expression of the two kinds of VEGF receptors. Increases endothelial nitric oxide synthase (eNOS) promoter activity and eNOS expression, increasing endothelial nitric oxide production. Vasorelaxation due to the inhibition of Ca(2+) influx through the Ca(2+) channel might be in part due to the inhibition of Ca(2+)-activated K(+) current and PGI(2) release. The incorporation of this phytomedicine into a composition provides at least 59 active principles in a single therapeutic.

*Hydrocotyle asiatica* (Gotu Kola, Bramhi, Pennywort, Marsh Penny, Pennywort; also *Hydrocotile asiatica asiatica*) contain terpenoids (triterpenes, asiaticoside, brahmoside and brahminosidea, (saponin glycosides) aglycones, asiaticentoic acid, centellic acid, centoic acid and madecassic acid), sesquiterpenes (caryophyllene, trans-B-farnesene), volatile oils (Germacrene D), alkaloids (hydrocotylin), flavones (Quercetin, kaempferol, sesquiterpenes, stigmasterol, and sitosterol), and vallerine, fatty acids, resin, and tannins *Hydrocotyle* improves microcirculation and decreases capillary permeability. Incorporation of this phytomedicine in a composition provides at least 59 active principles in a single therapeutic.

*Ruscus aculeatus* (Butcher's Broom, Box Holly, Jew's Myrtle, Knee Holly, Kneeholm, Pettigree, Sweet Broom) contains as primary active ingredients the steroidal saponins (ruscogenin and neoruscogenin), but other constituents have been isolated, including flavonoids, tetracosanoic acid, chrysophanic acid, sitosterol, campesterol, stigmasterol, triterpenes, coumarins, sparteine, tyramine, and glycolic acid. Its ingredients reduce vascular permeability, and have antielastic properties. *Ruscus* inhibits endothelial responses to cytokines during inflammatory and vascular disorders and exerts significant anti-inflammatory and anti-thrombotic activities. Protective effects on capillaries, endothelium, and smooth muscle. Reduces capillary fragility, and improves circulation. The incorporation of this phytomedicine in a composition provides at least 28 active agents.

*Vaccinium myrtillus* (European blueberry or bilberry, closely related to American blueberry, cranberry, and huckleberry) contains anthocyanosides such as: cianadins, malvidins, petunidins and peonidins. Other ingredients include arbutin, asperuloside, astragalin, beta-amyrin, caffeic-acid, catechin, chlorogenic-acid, cyanadin-3-O-arabinoside, dihydroxycinnamic-acid, epicatechin, epigallocatechin, epimyrtine, ferulic-acid, gallic-acid, gallocatechin, hydroquinone, hyperoside, isoquercitrin, lutein, coumaric-acids, m-hydroxybenzoic-acid, monotropein, myrtillin, myrtillol, myrtine, neomyrtillin, protocatechuic-acid, quercetins, quinic-acid, resinic-acid, syringic-acid, ursolic-acid and vanillic-acid. Evidence suggests that anthocyanosides may benefit as well as strengthen the walls of blood vessels, reduce inflammation, and stabilize collagen containing tissues. The anthocyanosides improve the activity of enzymes lactic dehydrogenase, glucose-6-phosphatase and phosphoglucomutase, each involved in processes of vascular damage. Anthocyanosides reduce the arterial deposits and stimulate the production of vasodilators, like prostaglandin (PG12), thus protecting the vascular wall. They have strong antioxidant properties, as well. *Vaccinium* decreases capillary permeability and produces endothelium-dependent arterial relaxation in coronary arteries. Incorporation of this phytomedicine provides at least 63 active principles in a single therapeutic.

EXAMPLE 2

Composition for Circulatory Disorders

A particularly preferred composition, also known as Circulat™, is shown in Table 1. Ratios reflect the concentration of active ingredient over the natural state, and the amounts provided are mg of extract. Obviously, the amount should be increased where the strength is reduced, and vice versa.

TABLE 1

Herbaria (Circulat ™)

| Active Agent | Ratio | Amount (mg) |
|---|---|---|
| Energy enhancers | | |
| *Eleutherococcus senticosus* root extract | 5:1 | 53.53 |
| *Rhaponticum carthamoides* root extract | 12:1 | 3.85 |
| *Panax ginseng* root extract | 5:1 | 10.71 |
| *Panax quinquefolius* root extract | 5:1 | 32.12 |
| *Pfaffia paniculada* (Suma) root extract | 4:1 | 21.41 |
| *Rhodiola rosea* root extract | 5:1 | 9.64 |
| Bio-Intelligence modulators | | |
| *Echinacea angustifolia* root extract | 6:1 | 1.34 |
| *Echinacea purpurea* root extract | 6:1 | 1.34 |
| *Ganoderma lucidum* extract | 6:1 | 32.12 |
| *Grifola frondosa* extract | 10:1 | 12.85 |
| *Hydrastis canadensis* root extract | 5:1 | 38.54 |
| *Petiveria alliacea* | 1:1 | 64.24 |
| *Sutherlandia frutescens* | 1:1 | 64.24 |
| *Tabebuia avellanedae* bark extract | 4:1 | 40.15 |
| *Uncaria tomentosa* root extract | 10:1 | 16.06 |
| Organization improvers | | |
| *Angelica sinensis* root extract | 5:1 | 64.24 |
| *Crataegus oxyacantha* fruit extract | 5:1 | 42.83 |
| *Croton lechleri* bark resin extract | 10:1 | 10.71 |
| *Ginkgo biloba* leaf extract | 50:1 | 19.49 |
| *Hydrocotyle asiatica* plant extract | 5:1 | 64.24 |
| *Ruscus aculeatus* root extract | 5:1 | 57.82 |
| *Vaccinium myrtillus* fruit extract | 5:1 | 38.54 |
| Total | | 700 mg |

EXAMPLE 3

Tolerance Study

A multicentric, retrospective study was made on 104 healthy volunteers to evaluate patient tolerance and potential side effects of the herbaria/natural combination. A capsule containing 800 mg of the herbaria of Table 1 was administered to each participant three times per day for five days. During that period they were evaluated by a physician, who registered any finding as well as symptoms reported by subjects. The average age of the participants was 41.2 years with a SD of 6.8 years. Gender was 46% female, 54% male. The average weight of the subjects was 72.8 kgm with a SD of 10.2 kgm. No undesirable effects were observed in 98 (94.2%) of the subjects. Six (5.8%) subjects reported minor undesirable effects. These results showed the non-toxicity and safety of the formulation. Similar non-toxicity and tolerance results have been obtained in the study included herein as Example 4.

EXAMPLE 4

Treatment of Angina Pectoris

The following is a summary of an efficacy study of Circulat™ for the treatment of Angina Pectoris.

Context: Stable angina pectoris (SAP) is a common disorder caused by an imbalance between myocardial oxygen demand and supply, due to severe atherosclerotic narrowing of one or more coronary arteries. The annual death rate in SAP patients is 1.6%-3.2%. As many as 15% of SAP patients fail to respond to therapy or are ineligible for further intervention, which indicates the need for new therapeutic alternatives. Circulat™ is a standardized synergistic plant extract combination formulated under the principles of Systemic Medicine for the treatment of micro and macro vascular disease.

Objective: asses the hypothesis that SAP patients improve under treatment with Circulat™, and determine whether the response can be predicted by baseline factors' analysis.

Design, Setting, and Participants: 83 patients with SAP from 7 Adaptogenic Medical Centers, in Venezuela, received ten Circulat™ capsules bi-daily (BID), during an 8-week treatment period. Canadian cardiovascular society (CCS) class was analyzed at baseline and after treatment. Patients were divided into two groups depending on response to therapy. Baseline factors were compared between the two groups in an attempt to find factors predisposing patients to treatment failure. Reports of adverse events were obtained at the end of the study.

Results: All patients completed the two months treatment. Response to therapy was seen in 84.3% of the patients ($p<0.05$). Among the responders, 25% improved two CCS classes. Anginal status did not worsen in any of the patients. Treatment was most effective among patients suffering from CCS class II angina pectoris. Results were significantly better in patients with Diabetes mellitus, Hypertension, users of Beta-adrenoceptor antagonists, Statins, Aspirin and users of oral antidiabetic agents ($p<0.01$, $p<0.05$, $p<0.01$, $p<0.05$, $p<0.01$, and $p<0.01$, respectively). None of the study's patients suffered any adverse events during the treatment with Circulat™. None of the patients died during the studied period.

Conclusions: These results confirm the efficacy and safety of the treatment with Circulat™ to reduce CCS class scores in patients with stable angina pectoris, particularly in patients suffering from angina CCS II. Effects of this treatment are thought to be caused, among others, by improvement of vascular endothelium function, angiogenesis and enhancement of tissue perfusion.

Since angina is a symptom of ischemic (or ischaemic) heart disease (IHD), a disease characterized by reduced blood supply to the heart muscle, it is reasonable to extrapolate the use of Circulat™ to treat IHD as well since—as demonstrated in Example 5 below—genes associated with IHD were modulated by Circulat.™ Finally, experiments are planned to show proof of concept for broader use of Circulat.™

EXAMPLE 5

Gene Expression Studies

Circulat™ has also been used to treat Diabetic Lesions. Circulat™ is comprised of a variety of plants that can be classified as one of three essential components: Energy (E), Bio-intelligence (I) and Organization (O), as shown in Table 1. In order to study the molecular nature of Circulat™ activity, the effects of the three components on gene expression levels in cultured human fibroblasts were studied using whole-genome microarrays and compared to the effects of the preparation as a whole.

Lyophilized water extracts from whole Circulat™ and its three constituents were added separately to culture media to final concentrations of 3 mcg per ml and human fibroblast cells MRC-5 were cultured at 37° C. for 16 hours. Control fibroblasts were cultured in parallel under same conditions without the addition of any extracts. Upon treatment, total RNA from cell lysates was isolated and used for microarray analysis. Treatments with whole Circulat™ and its three fractions as well as control experiments were carried out in triplicates yielding 15 samples that were processed independently.

Microarray analysis was performed in accordance with standard procedures using Affymetrix GeneChip Human Genome U133 Plus 2.0™ arrays. U133 Plus 2.0™ arrays provide full genomic coverage and contain probes for more than 47,000 unique transcripts corresponding to more than 38,500 human genes. Following hybridization and scanning, raw data in the form of image files were converted to gene expression values using Affymetrix GeneChip Operating Software™ (GCOS). GCOS utilizes MAS 5.0 algorithm for data normalization, background subtraction, estimation of nonspecific binding, calculation of detection p-values, and generation of "presence" calls. Two-tailed Student's t-test assuming unequal sample variance was used to identify genes that displayed significant changes in the mean expression levels between control and each of the treated samples with the t-test p-value less then 0.05 and the mean fold change of at least 2.

Active component concentrations in the whole Circulat™ extract are likely to be lower than those in extracts from separate fractions since the same total amount (weight) of the starting material was used for extract preparation. We therefore also considered genes that were regulated in the whole preparation less strongly (1.5. and 1.2 fold difference) but with higher significance value cutoffs (0.01 and 0.001 t-test p-value, respectively).

In addition, the efficiency of extraction and lyophilization procedures of complex herbal preparations is difficult to precisely control, and this may result in subtle differences in relative concentrations of active ingredients in individual components of Circulat™ and the whole preparation. While this may hinder quantitative comparison between the samples, qualitative changes in expression levels should nevertheless be well-preserved (i.e. expression levels should display the same trend in an individual fraction as in Circulat™ as a whole).

The copious data obtained herein are not shown, but are available on request, and instead only the highlights are discussed herein.

Analysis of the expression data identified several genes that were regulated between 1.2 and 2 fold in the whole preparation and followed the same trend as in individual fractions (Table 2). Only probes that were called "present" in at least three out of six independent measurements for each of the four treatment/control pairs were considered in these analyses.

TABLE 2

Gene Expression

| Test | Number of Genes with Significant Change in Expression |
| --- | --- |
| Component 1 | 87 genes |
| Component 2 | 96 genes |
| Component 3 | 24 genes |
| Components 1 + 2 + 3 added | 155 non redundant genes |
| Circulat ™ | 196 genes |

On a macro level it can be seen that the Circulat™ as a whole affected 41 more genes than the three components added. On the other hand, 64 genes that change significantly after Circulat™ treatment were not observed in any of the three individual fractions. The data in Table 2 demonstrates that (1) treatment of human fibroblast cells with either Circulat™ or its components results in marked changes in gene expression patterns; (2) significant interactions between active ingredients of Circulat™ exist resulting in a more complex pattern of gene expression in the complete preparation as compared to those of isolated components.

Genes affected by Circulat™ (Table 3) are involved in a variety of cellular processes including protein, nucleic acid, lipid and carbohydrate metabolism, regulation of transcription, response to endogenous and external stimuli and stress, signal transduction and cell communication, cell growth and proliferation, development, protein modification and biosynthesis, generation of precursor metabolites, energy and other.

Analysis of genes affected by Circulat™ also reveals that 26 of them have been previously implicated in various human diseases (Table 4). This raises the exciting possibility that Circulat™ could be effective for treatment of other conditions.

TABLE 3

Genes affected by Circulat (as a whole) but not by Individual Components

| Gene Symbol | Gene Title |
| --- | --- |
| PGK1 | Phosphoglycerate kinase 1 |
| KIAA1840 | KIAA1840 |
| CPEB2 | Cytoplasmic polyadenylation element binding protein 2 |
| MYO1A | myosin IA |
| — | Full length insert cDNA clone YZ04E02 |
| RTN1 | reticulon |
| — | Transcribed locus |
| ZNF117 | Zinc finger protein 117 (HPF9) |
| SEC61B | Sec61 beta subunit |
| AIG1 | androgen-induced 1 |
| — | Transcribed locus |
| NQO1 | NAD(P)H dehydrogenase, quinone 1 |
| SYN2 | synapsin II |
| C20orf32 | chromosome 20 open reading frame 32 |
| PARD6B | par-6 partitioning defective 6 homolog beta (C. elegans) |
| SLC9A3 | Solute carrier family 9 (sodium/hydrogen exchanger), member 3 |
| TPST1 | Tyrosylprotein sulfotransferase 1 |
| RNF111 | Ring finger protein 111 |
| CCDC36 | coiled-coil domain containing 36 |
| — | — |
| — | CDNA clone IMAGE: 5284125 |
| NIPSNAP3B | nipsnap homolog 3B (C. elegans) |
| RAB7 | RAB7, member RAS oncogene family |

TABLE 3-continued

Genes affected by Circulat (as a whole) but not by Individual Components

| Gene Symbol | Gene Title |
|---|---|
| RBBP6 | retinoblastoma binding protein 6 |
| ENTPD7 | ectonucleoside triphosphate diphosphohydrolase 7 |
| ASPHD2 | aspartate beta-hydroxylase domain containing 2 |
| ICA1L | islet cell autoantigen 1.69 kDa-like |
| TXNDC4 | thioredoxin domain containing 4 (endoplasmic reticulum) |
| AHSA2 | AHA1, activator of heat shock 90 kDa protein ATPase homolog 2 |
| NAPE-PLD | N-acyl-phosphatidylethanolamine-hydrolyzing phospholipase D |
| MGC14376 | hypothetical protein MGC14376 |
| SOCS3 | suppressor of cytokine signaling 3 |
| — | MRNA; cDNA DKFZp434G1972 (from clone DKFZp434G1972) |
| HOM-TES-103 | hypothetical protein LOC25900, isoform 3 |
| RBMS1 | RNA binding motif, single stranded interacting protein 1 |
| CCNL2///OC643556 | cyclin L2, similar to Aurora kinase A-interacting protein |
| — | CDNA FLJ34964 fis, clone NTONG2004095 |
| MRPL34 | mitochondrial ribosomal protein L34 |
| BCDIN3 | bin3, bicoid-interacting 3, homolog (*Drosophila*) |
| — | MRNA; cDNA DKFZp686D22106 (from clone DKFZp686D22106) |
| — | Full length insert cDNA clone YY61D04 |
| SMCHD1 | structural maintenance of chromosomes |
| FLJ11903 | similar to hypothetical protein MGC40405 |
| CDKN2C | cyclin-dependent kinase inhibitor 2C (p18, inhibits CDK4) |
| FAM76B | family with sequence similarity 76, member B |
| SEC15L2 | SEC15-like 2 (*S. cerevisiae*) |
| KIAA0701 | KIAA0701 protein |
| H2AFX | H2A histone family, member X |
| CCDC82 | coiled-coil domain containing 82 |
| LPP | LIM domain containing preferred translocation partner in lipoma |
| FANCB | Fanconi anemia, complementation group B |
| GTSE1 | G-2 and S-phase expressed 1 |
| HMGA1 | high mobility group AT-hook 1 |
| ATP5F1 | ATP synthase, H+ transporting, mitochondrial F0 complex, subunit B1 |
| SATB2 | SATB family member 2 |
| LOC401320 | Hypothetical LOC401320 |
| BRIP1 | BRCA1 interacting protein C-terminal helicase 1 |
| CNNM1 | cyclin M1 |
| UBE2E3 | Ubiquitin-conjugating enzyme E2E 3 (UBC4/5 homolog, yeast) |
| RFWD2 | Ring finger and WD repeat domain 2 |
| ADAM32 | ADAM metallopeptidase domain 32 |
| PQLC2 | PQ loop repeat containing 2 |

The large number of genes previously implicated in a variety of human diseases revealed by this study suggests some possible new uses for the Circulat™ preparation to treat the diseases listed in Table 4. The fact that Circulat™ changes expression level in these genes could indicate that it might also produce a positive clinical effect. However, clinical studies are planned to establish efficacy, although disease priorities have yet to be established.

TABLE 4

Disease-associated genes affected by Circulat ™ treatment

| Gene Symbol | OMIM Disease Description |
|---|---|
| PGK1 | Hemolytic anemia due to PGK deficiency |
|  | Myoglobinuria/hemolysis due to PGK deficiency |
| MYO1A | Deafness, autosomal dominant nonsyndromic sensorineural |
| PRKAR1A | Adrenocortical tumor, somatic |
|  | Carney complex, type 1 |
|  | Myxoma, intracardiac |
|  | Pigmented adrenocortical disease, primary isolated |
|  | Thyroid carcinoma, papillary |
|  | Systemic lupus erythematosus |
| AHI1 | Joubert syndrome-3 |
| NQO1 | Benzene toxicity, susceptibility to |
|  | Leukemia, post-chemotherapy, susceptibility to |
| SYN2 | Schizophrenia, susceptibility to |
| C4A | C4 deficiency |
|  | Blood group, Rodgers |
| UROD | Porphyria cutanea tarda |
|  | Porphyria, hepatoerythropoietic |
| WNK1 | Pseudohypoaldosteronism, type II |
| NR4A3 | Chondrosarcoma, extraskeletal myxoid |
| RAB7 | Charcot-Marie-Tooth disease, type 2B |
| IL6 | Osteopenia/osteoporosis |
|  | Kaposi sarcoma, susceptibility to |
| SAT | Keratosis follicularis spinulosa decalvans |
| SOCS3 | Dermatitis, atopic, 4 |
| PDE4D | Stroke, susceptibility to, 1 |
| SLC19A2 | Thiamine-responsive megaloblastic anemia syndrome |
| RAB3GAP1 | Warburg micro syndrome 1 |
| ENTH | Schizophrenia, susceptibility to |
| CD55 | Blood group Cromer |
| ALDOB | Fructose intolerance |
| LHX4 | Short stature, pituitary and cerebellar defects, and small sella turcica |
| VAPB | Amyotrophic lateral sclerosis 8 |
|  | Spinal muscular atrophy, late-onset, Finkel type |
| LPP | Leukemia, acute myeloid |
|  | Lipoma |
| HMGA1 | Lipoma |
| FANCB | Fanconi anemia, complementation group B |

TABLE 4-continued

Disease-associated genes affected by Circulat ™ treatment

| Gene Symbol | OMIM Disease Description |
|---|---|
| BRIP1 | Breast cancer, early-onset |
| | Fanconi anemia, complementation group J |
| CYP3A4 | Associated with cardia isquemia. |
| NMNAT2 | |

Very noteworthy (in Table 4) is the fact that Circulat™ has modulator effect on genes associated with cardiac ischemia: Gene CYP3A4-important for ATP production by oxidative phosphorilation; and Gene NMNAT2 involved in energy production by anaerobic glycolisis.

It is also evident that components 1 and 2 have the ability to regulate more genes than component 3 (87, 96 and 24 genes, respectively), suggesting that their contribution to the biological activity of Circulat™ is more important than that of component 3. This observation, while important, cannot be interpreted as the final proof of relative significance of the fractions, because we cannot assess the significance of contributions of individual genes at this point (i.e. it is possible that a contribution of one gene affected by fraction 3 may be more important than those of many genes affected by fractions 1 and 2).

Analysis of genes regulated by the whole Circulat™ and its individual components demonstrated the existence of significant interactions between active ingredients of Circulat™ suggesting that the full therapeutic effects can only be achieved by administration of the complete preparation.

Finally, additional preliminary clinical results point to very auspicious results in Ischaemic Heart Disease. The final results of which can be provided for further proof of Circulat™ value in IHD treatment.

EXAMPLE 7

Principles for Selecting Synergistic Combinations

In order to expand the range of formulations encompassed by the invention, we have classified beneficial plants into one of three categorized groups, each of which should be present for synergistic effect. The classifications are Energy, Bio-Intelligence and Organization. Plants classified under Energy are associated with ATP synthesis (such as the Krebs cycle, oxidative phosphorylation, beta-oxidation, etc.). Plants classified under Bio-Intelligence are those that regulate the neuroendocrine and immunological systems and cellular processes, thus controlling the interactions between the various systems in the body. Finally, plants classified under Organization are those that relate to the structure and function of specific organs. Combinations of plants from these three classification groups have synergistic effect because they address each necessary component of cellular and organic health-in effect they provide the triangle on which healing is fully supported.

A large group of plants were classified according to this system, based on what is known in the literature about their active ingredients and mode of action. The classification is presented in Table 5. Table 5 is representative only—based on the criterion described herein, additional plants can easily be categorized as their mode of action is elucidated.

Everything cited herein is expressly incorporated by reference and is relisted here for the convenience of the reader.

U.S. Pat. No. 7,303,772

Olalde J, et al., Clinical outcomes of diabetic foot management with Circulat, Phytotherapy, Res 22: 1292 (2008).

Antoshechkin A, et al., Analysis of Effects of the Herbal Preparation Circulat on Gene Expression Levels in Cultured Human Fibroblasts, Phytotherapy Res, 21: 777 (2007).

What is claimed is:

1. A method of treating ischemic heart disease, comprising administering an effective amount of a phytoceutical composition to a patient with ischemic heart disease, said phytoceutical composition comprising:

> *Eleutherococcus senticosus* root extract
> *Rhaponticum carthamoides* root extract
> *Panax ginseng* root extract
> *Panax quinquefolius* root extract
> *Pfaffia paniculate* (Suma) root extract
> *Rhodiola rosea* root extract
> *Echinacea angustifolia* root extract
> *Echinacea purpurea* root extract
> *Ganoderma lucidum* extract
> *Grifola frondosa* extract
> *Hydrastis canadensis* root extract
> *Petiveria alliacea*
> *Sutherlandia frutescens*
> *Tabebuia avellanedae* bark extract
> *Uncaria tomentosa* root extract
> *Angelica sinensis* root extract
> *Crataegus oxyacantha* fruit extract
> *Croton lechleri* bark resin extract
> *Ginkgo biloba* leaf extract
> *Hydrocotyle asiatica* plant extract
> *Ruscus aculeatus* root extract, and
> *Vaccinium myrtillus* fruit extract.

2. The method of claim 1, said composition comprising:

| | |
|---|---:|
| *Eleutherococcus senticosus* root extract | 53.53 mg |
| *Rhaponticum carthamoides* root extract | 3.85 mg |
| *Panax ginseng* root extract | 10.71 mg |
| *Panax quinquefolius* root extract | 32.12 mg |
| *Pfaffia paniculata* (Suma) root extract | 21.40 mg |
| *Rhodiola rosea* root extract | 9.64 mg |
| *Echinacea angustifolia* root extract | 1.34 mg |
| *Echinacea purpurea* root extract | 1.34 mg |
| *Ganoderma lucidum* extract | 32.12 mg |
| *Grifola frondosa* extract | 12.85 mg |
| *Hydrastis canadensis* root extract | 38.54 mg |
| *Petiveria alliacea* | 64.24 mg |
| *Sutherlandia frutescens* | 64.24 mg |
| *Tabebuia avellanedae* bark extract | 40.15 mg |
| *Uncaria tomentosa* root extract | 16.06 mg |
| *Angelica sinensis* root extract | 64.24 mg |
| *Crataegus oxyacantha* fruit extract | 42.83 mg |
| *Croton lechleri* bark resin extract | 10.71 mg |
| *Ginkgo biloba* leaf extract | 19.49 mg |
| *Hydrocotyle asiatica* plant extract | 64.24 mg |
| *Ruscus aculeatus* root extract | 57.82 mg |
| *Vaccinium myrtillus* fruit extract | 38.54 mg | or equivalent ratios thereof.

3. A method of treating angina pectoris, comprising administering an effective amount of a phytoceutical composition to a patient with angina, said composition comprising:

> *Eleutherococcus senticosus* root extract
> *Rhaponticum carthamoides* root extract
> *Panax ginseng* root extract
> *Panax quinquefolius* root extract
> *Pfaffia paniculate* (Suma) root extract -continued Rhodiola rosea root extract
Echinacea angustifolia root extract
Echinacea purpurea root extract
Ganoderma lucidum extract
Grifola frondosa extract
Hydrastis canadensis root extract
Petiveria alliacea
Sutherlandia frutescens
Tabebuia avellanedae bark extract
Uncaria tomentosa root extract
Angelica sinensis root extract
Crataegus oxyacantha fruit extract
Croton lechleri bark resin extract
Ginkgo biloba leaf extract
Hydrocotyle asiatica plant extract
Ruscus aculeatus root extract, and
Vaccinium myrtillus fruit extract.

or equivalent ratios thereof.

4. The method of claim 3, said composition comprising:

| | |
|---|---|
| Eleutherococcus senticosus root extract | 53.53 mg |
| Rhaponticum carthamoides root extract | 3.85 mg |
| Panax ginseng root extract | 10.71 mg |
| Panax quinquefolius root extract | 32.12 mg |
| Pfaffia paniculata (Suma) root extract | 21.40 mg |
| Rhodiola rosea root extract | 9.64 mg |
| Echinacea angustifolia root extract | 1.34 mg |
| Echinacea purpurea root extract | 1.34 mg |
| Ganoderma lucidum extract | 32.12 mg |
| Grifola frondosa extract | 12.85 mg |
| Hydrastis canadensis root extract | 38.54 mg |
| Petiveria alliacea | 64.24 mg |
| Sutherlandia frutescens | 64.24 mg |
| Tabebuia avellanedae bark extract | 40.15 mg |
| Uncaria tomentosa root extract | 16.06 mg |
| Angelica sinensis root extract | 64.24 mg |
| Crataegus oxyacantha fruit extract | 42.83 mg |
| Croton lechleri bark resin extract | 10.71 mg |
| Ginkgo biloba leaf extract | 19.49 mg |
| Hydrocotyle asiatica plant extract | 64.24 mg |
| Ruscus aculeatus root extract | 57.82 mg |
| Vaccinium myrtillus fruit extract | 38.54 mg. |

* * * * *